US006595920B2

(12) United States Patent
Walton

(10) Patent No.: US 6,595,920 B2
(45) Date of Patent: Jul. 22, 2003

(54) NON-CONTACT INSTRUMENT FOR MEASUREMENT OF INTERNAL OPTICAL PRESSURE

(75) Inventor: Eric K. Walton, Columbus, OH (US)

(73) Assignee: The Ohio State University, Columbus, OH (US)

(*) Notice: Subject to any disclaimer, the term of this patent is extended or adjusted under 35 U.S.C. 154(b) by 145 days.

(21) Appl. No.: 09/862,431

(22) Filed: May 21, 2001

(65) Prior Publication Data

US 2002/0173711 A1 Nov. 21, 2002

(51) Int. Cl.[7] ................................................. A61B 3/16
(52) U.S. Cl. ....................................... 600/401; 600/402
(58) Field of Search ................................. 600/400, 401, 600/402, 405

(56) References Cited

U.S. PATENT DOCUMENTS

| | | | |
|---|---|---|---|
| 4,367,552 A | | 1/1983 | Jacobson |
| 4,745,606 A | | 5/1988 | Uehara et al. |
| 4,928,697 A | | 5/1990 | Hsu |
| 5,002,056 A | * | 3/1991 | Takahashi et al. ........... 600/401 |
| 5,076,274 A | * | 12/1991 | Matsumoto .................. 600/401 |
| 5,148,807 A | | 9/1992 | Hsu |
| 5,251,627 A | * | 10/1993 | Morris ......................... 600/398 |
| 5,325,380 A | | 6/1994 | Clendening et al. |
| 5,438,416 A | | 8/1995 | Nater |
| 5,708,672 A | | 1/1998 | Pessot et al. |
| 5,732,095 A | | 3/1998 | Zorabedian |
| 5,828,454 A | | 10/1998 | Gust |
| 5,963,568 A | | 10/1999 | Paoli |

OTHER PUBLICATIONS

"Home tonometer is as reliable as in–office machine", Ocular Surgery News, Mar. 15, 1997 (1 page).
Zeimer Self–Tonometer (2 pages), before Sep. 2, 1998.
Report #20, Non–Contact laser Interferometric Tonometer (NCLIT) Study, May 31, 1998, Project Bibliography (27 pages).
U.S. patent application Ser. No. 08/757,346, filed Nov. 27, 1996 for Laser Interferometer Having Multiple Sensors, now abandoned (175 pages).
Piltz, et al. "Momentary Fluctuations of Intraocular Pressure in Normal and Glaucomatous Eyes", Amer. Jour. of Ophthal, 99:333–339, Mar. 1998.
Shiose Y. "Intraocular Pressure: New Perspectives", Surv. Opthalmol, vol. 34: pp. 413–435, 1990.
Schulzer M. and Drance S.M. "Intraocular Pressure, Systemic Blood Pressure, and Age: A Correlational Study", Brit. J. of Ophthal, vol. 71, pp. 245–249, 1987.
Herndon L. W. et al., "Central Corneal Thickness in Normal, Glaucomatous, and Ocular Hypertensive Eyes", Arch Ophthalmol, vol. 115, pp. 1137–1141, Sep. 1997.

\* cited by examiner

*Primary Examiner*—Andrew M. Dolinar
(74) *Attorney, Agent, or Firm*—Emch, Schaffer, Schaub & Porcello Co., L.P.A.

(57) ABSTRACT

A method and apparatus for measuring the intraocular pressure of a cornea includes an interferometer directing a beam of a coherent light along a path to the cornea, a sensor for sensing the reflected light from the cornea, an air supply device for directing puffs of air to the cornea in alignment with the beam to cause the surface of the cornea to be artificially displaced and means for measuring variations of light intensity reaching the sensor.

11 Claims, 5 Drawing Sheets

NON-CONTACT INSTRUMENT FOR MEASUREMENT OF INTERNAL OPTICAL PRESSURE

BACKGROUND OF THE INVENTION

The present invention is directed toward an improved instrument for use in providing an accurate measurement of the intraocular pressure (IOP) of an eye without making any physical contact with the eye and without need for eye drops or anesthetic. The instrument of the present invention achieves these measurements through non-invasive and non-contact techniques, thereby providing an improved method for use in the early detection of glaucoma.

Glaucoma is an eye disease which can damage the optic nerve and which is one of the leading causes of blindness in the U.S. and throughout the world. Two out of every one hundred persons over age 35 have vision threatened by glaucoma.

When an object is viewed, the image is carried from the retina of the eye to the brain by the optic nerve. The optic nerve is an accumulation of over one million individual transmitters, each carrying a message to the brain. The individual messages all join together to provide side vision or peripheral vision as well as sharp central vision. Glaucoma can permanently damage the optic nerve, causing blind spots in areas of vision to develop. If glaucoma is undiagnosed, the optic nerve may sustain considerable irreversible damage and may even be destroyed, resulting in blindness.

Glaucoma is detectable by measuring the intraocular fluid pressure at the front surface or cornea of the eye. Intraocular fluid flows through the inner eye continuously to maintain the structure of the eye, in particular, the cornea. If the outflow or drainage system within the eye becomes blocked for any reason, the fluid backs up within the inner eye causing the intraocular fluid pressure to increase, thereby increasing the potential for damage to the optic nerve. The primary preventative measure which can be taken is the early detection of glaucoma by periodic testing of the intraocular pressure (IOP) since an elevated intraocular pressure (IOP) is clearly basic to the whole concept of glaucoma.

A variety of devices have been devised to facilitate the measurements of the intraocular pressure. The most common is a tonometer which measures the force necessary to applanate or flatten a given area of the cornea. An adjustable known force is applied to flatten a predetermined area of the cornea. This permits a direct measure of pressure to be made because the force and the area are directly known. The most common unit of this type is the Goldmann tonometer. While accurate in its measurements, the Goldman tonometer is an undesirable tool for many reasons. It is designed to provide a single time-segregated measurement of intraocular pressure. The application-type tonometer must be used with a topical anesthetic and a fluorescein dye. It includes physical touching of the eye, which many patients find objectionable. There is also an inherent risk of abrasion, injury, or infection to the eye as a result of contact.

Another common tonometer apparatus is the Schiotz or plunger-type tonometer. The Schiotz tonometer is placed before the eye along the optical axis and a plunger is released which flattens the cornea to a specified diameter and measures the forces applied. The Schiotz tonometer has the same undesirable qualities as the Goldman tonometer. It has been found that the patient usually has a somewhat high level of fear and physical discomfort as a result of such eye contact. Thus, the patient will tend to avoid the procedure, if possible.

A new generation of tonometers have been designed in an effort to limit physical contact with the eye which utilize a very strong air puff that impacts the eye. The air puff impinges on the cornea causing a sudden curvature reduction, applanation, and finally a slight concavity before restoration. Patient objections are still encountered when using the air puff system due to the discomfort caused by the force of the air puff on the eye and the accompanying audible explosion of the air puff as it is generated. Other disadvantages include the fact that an air puff measurement is a one-time occurrence and may, therefore, be offset from the actual average pressure value.

Other types of non-contact tonometers are disclosed in U.S. Pat. Nos. 4,928,697 and 5,148,807 both of which are assigned to the assignee of the present invention. The tonometers disclosed in those patents utilize the principles of induced phase modulation and/or frequency modulation of optical or acoustic waves which are directed toward the cornea as a diagnostic beam. The high frequency diagnostic waves are transmitted either as high frequency sonic waves or visible or invisible light waves.

Another non-contact instrument for measuring displacement of the cornea is disclosed in a thesis of Theodore Trost entitled Laser Interferometer Having Multiple Sensors which was published in 1995 and was available at The Ohio State University Library. As disclosed in that thesis, there is provided an interferometric displacement measurement apparatus having a coherent laser beam incident upon a partially reflective mirror, forming a measurement beam which is reflected back onto a sensor field. The incident beam also forms a reference beam incident upon the sensor field. The sensor field comprises at least two and preferably three or more photodetecting sensors spaced radially of the measurement beam axis arriving at the sensor field.

The interferometer disclosed is theoretically designed to measure the relative displacement of a target surface such as the surface of the cornea.

The Trost interferometer has many deficiencies and was not successfully reduced to practice. Problems were encountered in translating the relative displacement of the surface of the cornea to provide meaningful measure of intraocular pressure. There is ambiguity in determining the absolute direction of movement of the cornea surface and problems in eliminating excessive ambient noise received and measured by the system. Finally, measurements taken by the Trost apparatus are found to bear no statistical relationship to like measurements taken by a Goldman apparatus.

Most recently, an interferometer utilizing optical modulation to measure optical displacement has been patented to Gust (U.S. Pat. No. 5,828,454). Gust teaches the measurement of the static and dynamic displacement of a cornea by measuring the phase shift of an optical pathway. While the Gust patent is predicated on the theory that the measured phase shift is linearly proportional to deflection of the cornea, recent research has established that such a direct correlation is not necessarily as simple and accurate as Gust presents.

For instance, the eye has a multiplicity of reflective surfaces such as the lens, iris, front surface of the tear layer and the corneal surface. If the optical beam is not properly focused, it cannot be accurately predicted which surface is reflecting the beam, thus reducing the dependability and reliability of the instrument.

These and other non-contact tonometer attempts to make use of light waves and sound waves to measure corneal displacement have all suffered from two major deficiencies: the inability to accurately focus the measurement beam on the cornea and align the measurement beam with the sensor. Many complicated physical and mathematical techniques designed to meet and overcome these techniques have contravened the goal of simplicity in obtaining an accurate measurement of intraocular pressure by means of a non-contract tonometer.

Therefore, it is an object of the invention to provide an accurate non-invasive method and apparatus for performing the method of measuring the intraocular pressure of an eye.

A further object of the invention is to provide a method and apparatus for performing the measurement of the intraocular pressure of an eye continuously for a selected period of time in order to view variations in the pressure over time.

Yet another object of the present invention is to apply diagnostic energy to the cornea in a controlled, non-invasive, direct manner to accurately focus the energy onto a desired surface of the eye.

Yet another object of the invention is to provide a non-contact tonometer that can be adopted for use in an office or hospital on a fixed stand or, alternatively, be provided as a portable unit for use by health care professionals working, for instance, in nursing homes and assisted living homes, or be provided as a portable home unit simple enough to be used by individuals with little or no health care training.

It is a final object of the present invention to provide an instrument which accurately measures the intraocular pressure through non-invasive and non-contact type techniques.

IN THE DRAWINGS

DETAILED DESCRIPTION

Figure 1:
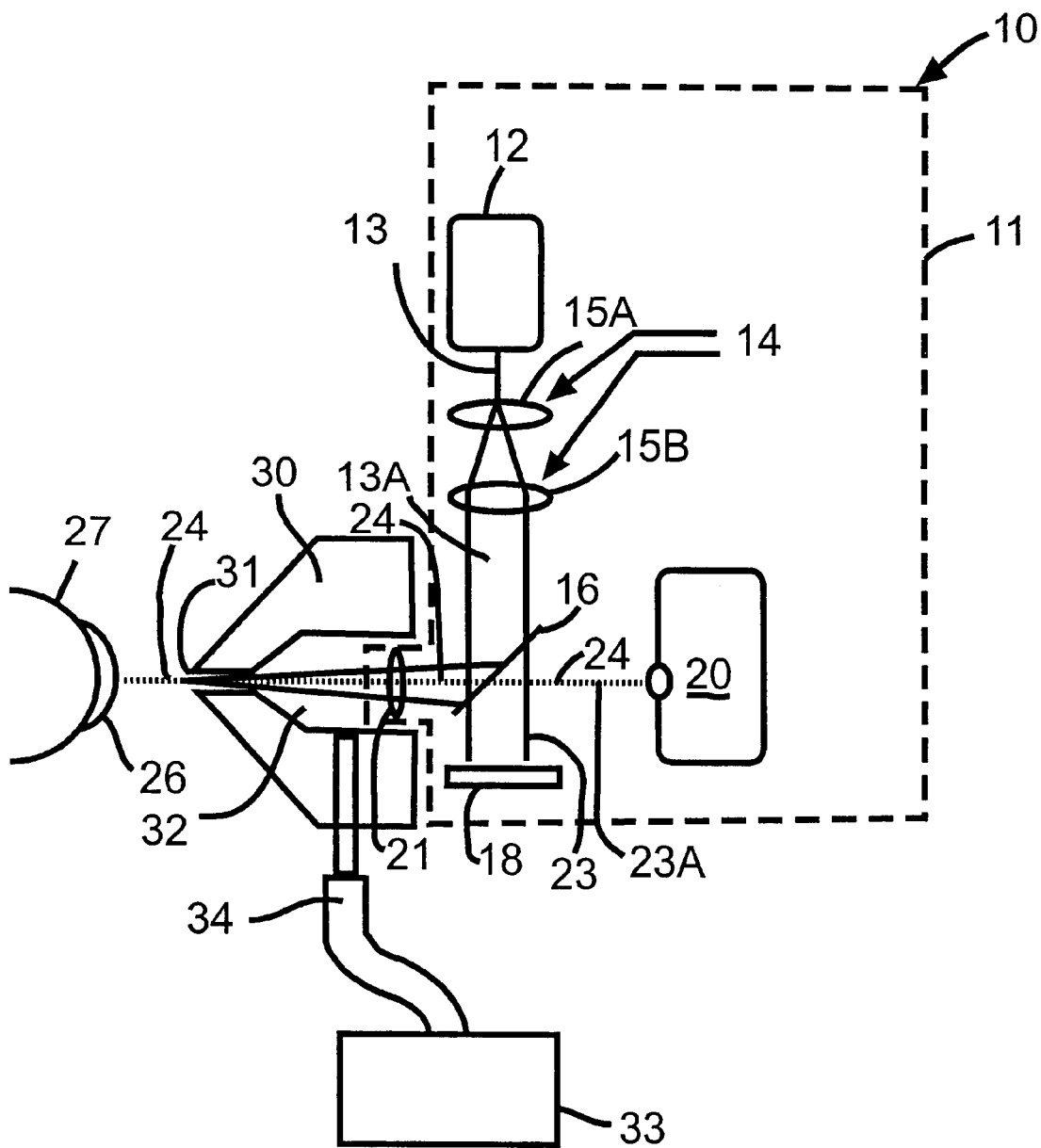
FIG. 1 is a schematic view showing apparatus of the present invention.
Figure 2:
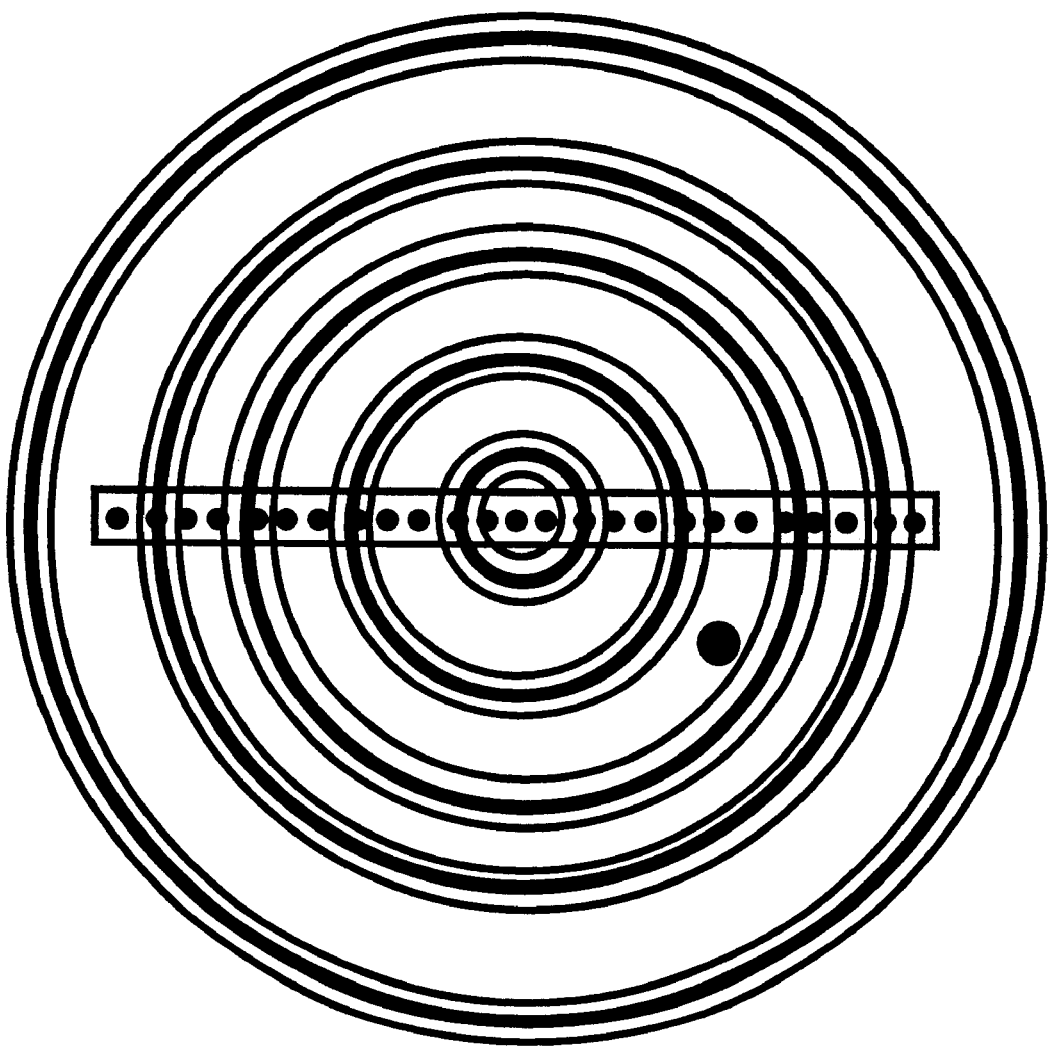
FIG. 2 is a schematic showing a pattern of ring signals created by the interferometer of the present invention and a centered one dimensional linear array of optical detectors serving as the sensor of the present invention and a representation of a single optical detector sensor or a sensor having a small number of juxtaposed optical detectors.

Referring to the drawings, there is shown in FIG. 1 an interferometer generally designated by the numeral 10 comprising a laser 12, a beam expander 14 and a beam splitter 16 mounted on the housing 11. The laser 12 may be one of a number of well known types such as, for example, a helium-neon laser or a diode laser. The laser envisioned for use with the invention is classified as either a Class 1 or Class 2A laser under the American National Standards Institute's (ANSI) Z136.1 Safety Use of Lasers standard. This "no hazard" classification allows a patient to be safely viewed by the laser for up to 1000 seconds or at least 15 minutes in a single setting without risk of ocular damage. The laser 12 emits a beam 13 which passes through the beam expander 14 comprising first and second lens 15A and 15B to form the expanded beam 13A. The expanded beam 13A passes through a beam splitter 16 which divides it into two beams, namely, a reference beam 23 and a measurement beam 24. The reference beam 23 is reflected from a mirror 18 back to the beam splitter 16 which in turn reflects the reference beam back to a sensor system 20 as a reflected beam 23A. Preferably the sensor system 20 is a one dimensional linear array of pixels as shown in FIG. 2.

Figure 3:
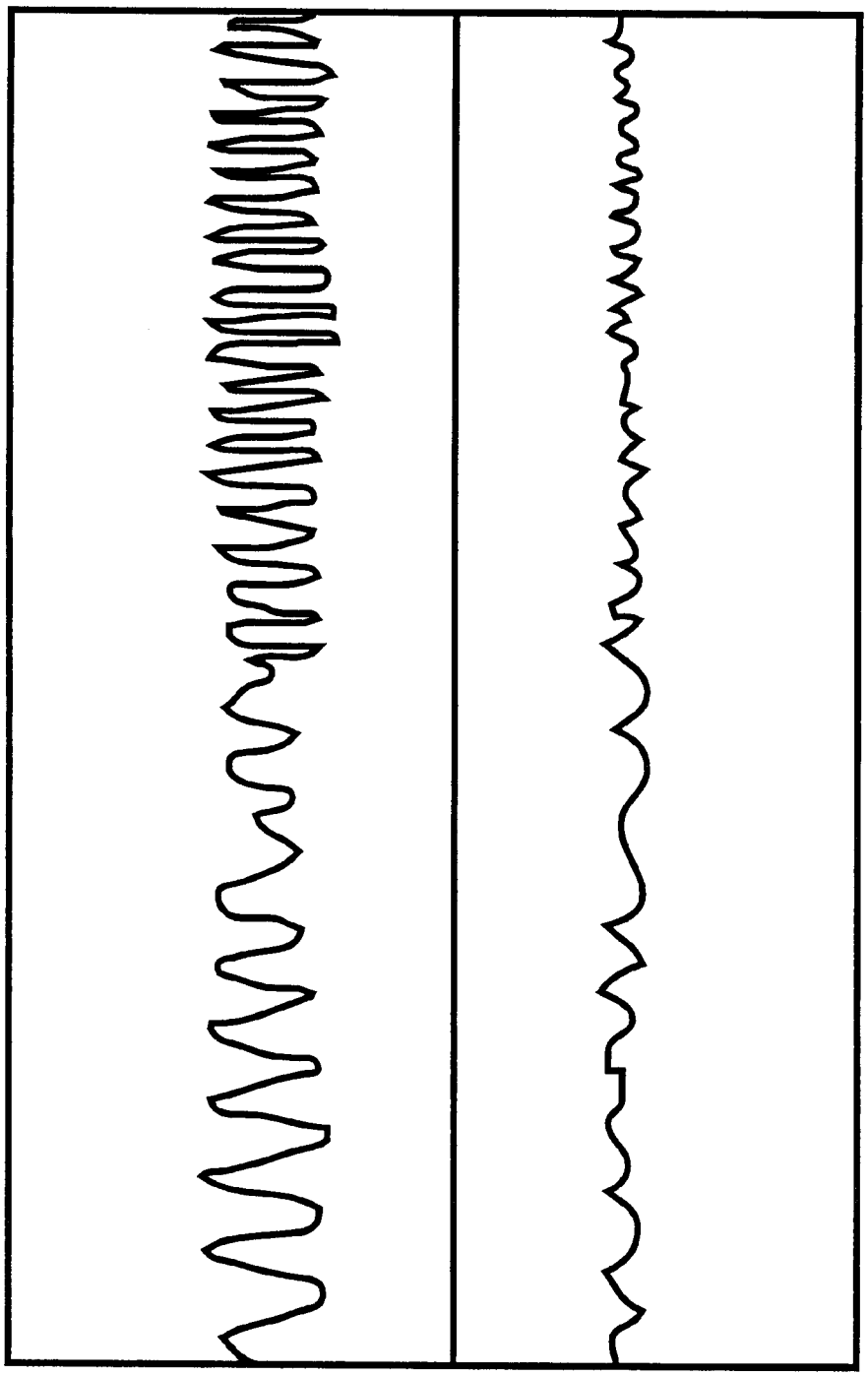
FIG. 3 is a graph showing the output received from two sensors caused by motion of the cornea as tested by the non-contact tonometer of the present invention.

The measurement beam 24 passes through a lens 21 which causes it to converge upon the surface of the cornea 26 of the eye 27 being tested. The measurement beam 24 is reflected back from the surface of the cornea 26, through the beam splitter 16 to the sensor system 20. Interference between the measurement beam 24 and the reflected beam 23A creates an interference fringe pattern of rings on the surface of the sensor system 20. As the surface of the cornea 26 is displaced toward or away from the sensors of the sensor system 20, the interference rings expand outwardly from a ring center or contract inwardly toward a ring center. The propagating rings pass over the sensors which convert the variations in the light intensity to proportional variations in voltage, thus causing an output, as shown in FIG. 3, for two sensors that varies from high to low as the illumination varies from bright to dark.

Figure 4:
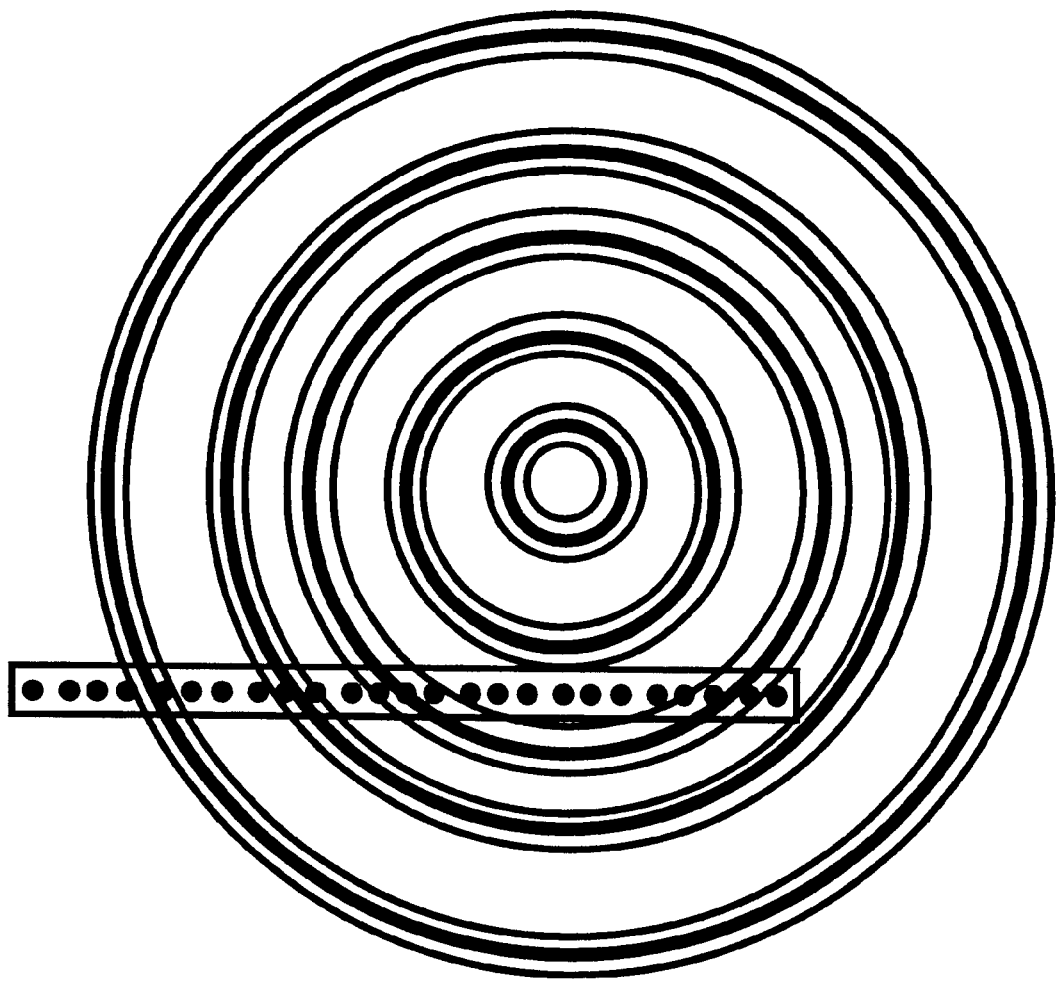
FIG. 4 is a schematic showing the linear array sensor of FIG. 2 in a non-aligned position.

The output signal of the sensor system 20 generates a voltage that is proportional to the varying light intensity as the rings pass over it. A transition from dark to light and back to dark corresponds to a target surface displacement of one-half optical wavelength along the direction of the beam between the surface of the cornea 26 and the sensors. Therefore, the number of rings passing over the sensor system 20 is a function of the displacement, which permits calculation of the displacement of the cornea 26 relative to the sensor 20. Viewing FIG. 2, a horizontal one dimensional linear array is shown in comparison with prior art single point sensors or sensor clusters. It has been found that a horizontal one dimensional linear sensor array serves to represent the movement and pattern of the fringe rings more completely than prior art single sensors and sensor clusters. For instance, if the sensor array is not in direct alignment with the interferometer ring patterns, as shown in FIG. 4, accurate processing of the resultant shifted output pattern is still possible because the misalignment only causes a position shift of the sensor output pattern. A single sensor or sensor cluster is more easily misaligned with the ring pattern often falling entirely away from the sensor. Thus, the use of a horizontal linear array of sensors greatly simplifies the alignment issues for the tonometer of this invention.

Extending from the housing 11 of the interferometer system 10 is a nozzle 30 having an outlet orifice 31 intended to be aligned with and spaced from the surface of the cornea 26 of the patient being examined. The nozzle 30 has an inlet passageway 32 which is connected to an air puff supply system 33 by means of tube 34. The air puff supply system 33 pulses the air directed to the nozzle such that it exits the outlet orifice 31 onto the surface of the cornea 26 with a periodic rhythm of between 5 to 100 Hertz. The nozzle 30 emits the puffs coaxially with the measurement beam 24 from the interferometer 10 so that the cornea is struck with a periodic sequence of air puffs along the same axis of alignment as the measurement beam 24. The measurement beam 24 is thus monitoring the region on the cornea 26 which is directly deflected by the air puff force. The periodic string of puff pulses is preferably created by a reciprocating pump operating between 5 and 100 Hertz and preferably in the range of 30 to 60 Hertz. It has been found that, if the puff rate is less than 10 Hertz, normal human motion which commonly ranges from 2–20 Hertz will cause the surface of the cornea to move in the same periodic domain as the puff rate, thereby overlapping the puff rate period and making post processing of the sensor output difficult. On the other hand, if the puff rate is greater than 100 Hertz, the physical dynamics of the cornea will resist oscillation and inhibit it from responding to the puffs, thereby inhibiting accurate deflection and measurement of the corneal surface.

It is important that the measurement beam 24 be properly aligned with the cornea 26. If it is not properly aligned, the sensor system 20 cannot accurately provide fringe signals for processing. The alignment accuracy is preferably within a tolerance of +0.5 mm.

Figure 5:
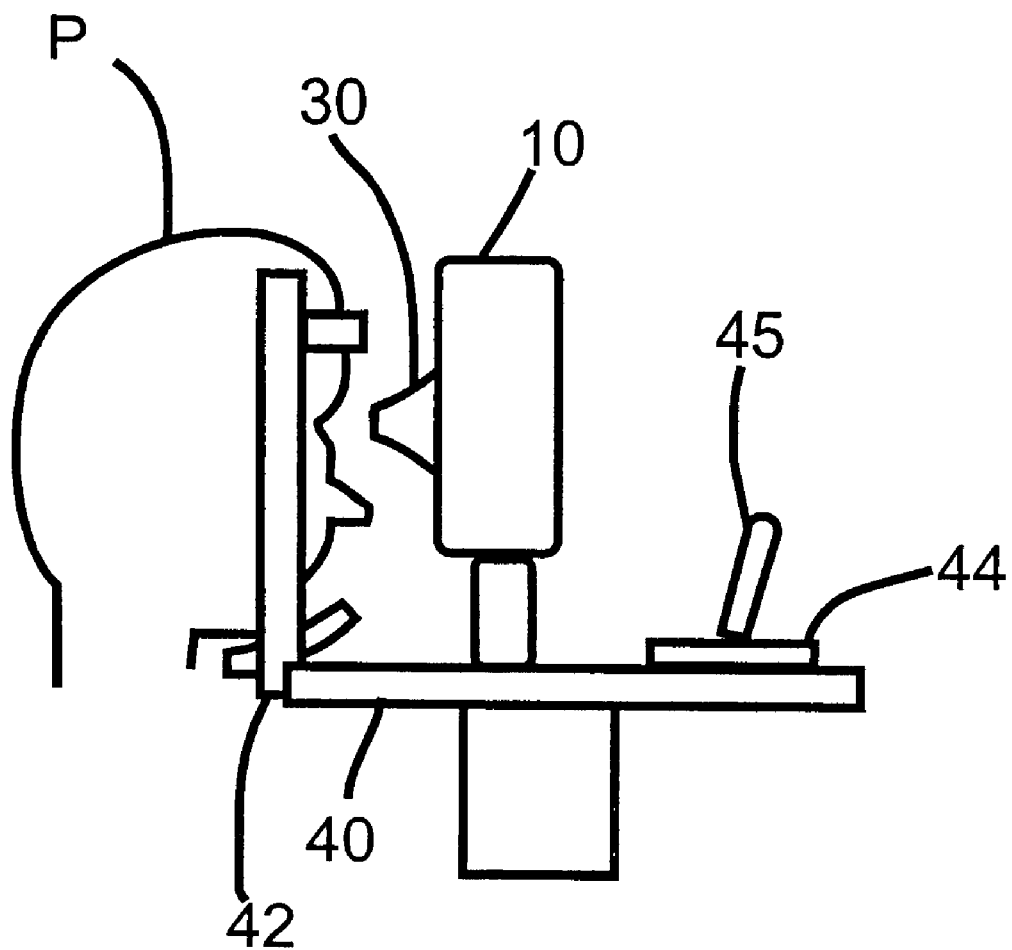
FIG. 5 is a schematic view of a system for aligning the interferometer of FIG. 1.

Referring to FIG. 5, there is shown schematically a system for aligning the interferometer 10 such that the measurement beam 24 and the nozzle 30 are properly aligned with the cornea 26 during the measurement process. There is provided a horizontal support 40 having mounted thereon a combined chin rest and head rest 42 for supporting the head of the subject S being tested. The interferometer system 10 is supported on the support 40 in a position such that the nozzle 30 will be generally aligned with the cornea 26 of the subject S whose head is supported in the chin/head rest 42. In order to move the interferometer system 10 and the nozzle 30 extending from its housing 11, there is provided a conventional knob 44 for effecting vertical adjustments and a controller 45 which may be moved left or right to effect, in cooperation with the knob 44, for alignment of the measurement beam 24 of the interferometer system 10 with the cornea 26. The controller 45 or other conventional adjustment mechanism may also effect movement of the interferometer system 10 toward and away from the cornea 26 to ensure proper spacing of the outlet orifice 31 from the surface of the cornea 26.

In order to determine when the interferometer system is properly aligned with the cornea 26, there may be provided a system of amplifiers and speakers or, preferably, a computer. In the simplest embodiments utilizing the speakers, the speakers are attached to an amplifier such that the input to the amplifier is a signal proportional to the brightness of the reflected measurement beam 24. Variations in such reflected measurement beam 24 due to normal uncontrolled motion are on the order of 500 to 3000 cycles per second. This is a Doppler effect and, in this case, the oscillations are in the normal range of human hearing. When the measurement beam 24 is properly aligned with the cornea 26, the sensor system 20 and amplifier will cause the speakers to give off a warbling tone thereby indicating that interferometer 10 and the sensor system 20 are in proper alignment. Normally it is possible to achieve this alignment indication in 10 to 20 seconds and to hold the system in alignment for nearly a minute.

The measured raw data is the light intensity of the reflected measurement beam illuminating the sensors of the sensor system 20. The light intensity on the sensor varies rapidly when the cornea relative velocity is large, and varies slowly when the cornea relative velocity is small. Once the measurements have been taken on a person, the raw data consists of a set of rapidly oscillating voltages.

If a single sensor or a small number of sensors are used, then the signal processing usually involves taking a running spectral estimation (as a function of time). The frequency of oscillation is directly proportional to the relative speed of the cornea. There is a directional ambiguity in these results, however.

If an array sensor, such as that shown in FIGS. 2 and 4, is used, then a pattern of moving light and dark lines emerges from the data. These light and dark moving patterns provide information about the motion of the interferometer rings even if the sensor is offset as in FIG. 4. The in and out motion of the interferometer rings is directly proportional to the axial deflection of the cornea.

The time history of the displacement of the cornea permits the displacement of the cornea due to the periodic air puff to be separated from the displacement due to random human motion. It is the induced displacement of the cornea resulting from periodic air puffs that is related to the intraocular pressure.

The present invention permits the measurement of cornea deflection as a function of time. This is done by extracting the beam interference frequency which is the periodic oscillation of the optical brightness caused by the interferometric interaction between the reference beam and the beam reflected from the cornea. A plot of this value as a function of time provides the speed of the cornea as a function of time. If the speed is then integrated, it is possible to obtain a measure of the cornea deflection as a function of time. The signal may then be filtered in such a way as to separate the background human motion induced signals from the periodic puff induced signals. From the puff induced cornea displacement, intraocular pressure may be computed based upon calibration experiments that establish the relationship between intraocular pressure and the cornea displacement.

The present invention provides a non-contact instrument as a small unit which can be mounted on a support which can be easily adjusted for alignment using a joy stick or other convenient positioning system. Additionally, it may be constructed in a sufficiently small package that it can be attached to a slit-lamp eye inspection unit for convenient use during a conventional eye exam. The method of operation of the instrument of the present invention permits accurate alignment of the unit with the cornea.

Many modifications will become readily apparent to those skilled in the art. Accordingly, the scope of the present invention should be determined only by the scope of the claims appended thereto.

I claim:

1. A method for measuring the intraocular pressure of a cornea of an eye, the cornea having an outwardly facing surface comprising the steps of:
    (a) directing at least one coherent light beam along a path to the cornea surface;
    (b) directing puffs of air or other gaseous fluid to the cornea surface at puff rates of between 5 hertz to 100 hertz to cause the cornea surface to be displaced;
    (c) reflecting the beam from the cornea surface to a sensor;
    (d) measuring variations of light intensity reaching the sensor and ascertaining therefrom the induced deflection of the cornea;
    (e) separating signals based upon the displacement of the cornea from the puffs of air set forth in step (b) from signals based upon displacement of the cornea from random human motion; and
    (f) calculating therefrom the intraocular pressure.

2. The method according to claim 1 further including the step of directing the puffs of air co-axially with the path of the coherent light.

3. The method according to claim 1 further including the step of focusing and aligning the beam on the cornea and aligning the puffs of air with the beam.

4. The method according to claim 3 wherein the focusing and aligning step includes:

measuring the intensity of light reaching the sensor during a period when no puffs of air or other gaseous fluid are being directed to the cornea;

detecting variations in such intensity during the period; and adjusting the focus and alignment of the beam with the cornea surface based upon the variations of intensity.

5. The method according to claim 3 wherein the focusing and aligning step includes:

measuring the intensity of light reaching the sensor during a period when no puff of air or other gaseous fluid is being directed to the cornea;

detecting variations in such intensity during the period;

creating computer generated signals based upon the variations in intensity to derive corrections to the alignment and focus of the beam; and using the computer generated corrections to adjust the focus and alignment of the beam with the cornea surface based upon the variations of intensity.

6. The method according to claim 3 wherein the focusing and aligning step includes:

providing an amplifier with speakers connected thereto;

thereafter, during a period when no puffs of air or other gaseous fluid are being directed to the cornea, measuring the intensity of light reaching the sensor;

detecting variations in such intensity during the period;

generating signals to the amplifier based upon the variations in intensity; and adjusting the focus and alignment of the beam with the cornea surface based upon sounds emanating from the speakers as a result of the signal applied to the amplifier.

7. The method according to claim 1 further including the step of measuring oscillations of optical brightness resulting from deflections of the cornea as a function of time.

8. Apparatus for measuring intraocular pressure of a cornea of an eye, comprising in combination (a) an interferometer directing a beam of coherent light along a path to the cornea;

(b) a sensor for sensing reflections of the beam from the cornea;

(c) an air supply device for directing puffs of air or other gaseous fluid to the cornea at puff rates of between 5 hertz to 100 hertz to cause the surface of the cornea to be displaced;

(d) means or separating (i) signals based upon the displacement of the cornea surface resulting from the puffs of air from (ii) signals based upon displacement of the cornea from random human motion; and (e) means for measuring variations of light intensity reaching the sensor and ascertaining therefrom the speed of movement of the cornea.

9. Apparatus according to claim 8 wherein the air supply means directs the puffs of air co-axially with the path of said coherent light beam.

10. Apparatus according to claim 8 wherein the beam is focused and aligned with the cornea and the air supply device aligns the puffs of air with the beam.

11. The apparatus of claim 8 wherein the sensor is a one dimensional linear array of pixels.

* * * * *